(12) United States Patent
Deck et al.

(10) Patent No.: US 9,295,418 B2
(45) Date of Patent: Mar. 29, 2016

(54) METHOD AND DEVICE FOR PUNCTURE OF INSERTION NEEDLE INTO SUBCUTANEOUS FATTY TISSUE

(71) Applicant: Roche Diagnostics Operations, Inc., Indianapolis, IN (US)

(72) Inventors: Frank Deck, Niederkirchen (DE); Karl-Peter Ebert, Fraenkisch-Crumbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 272 days.

(21) Appl. No.: 13/737,661

(22) Filed: Jan. 9, 2013

(65) Prior Publication Data

US 2013/0131467 A1 May 23, 2013

Related U.S. Application Data

(63) Continuation of application No. PCT/EP2011/003140, filed on Jun. 24, 2011.

(30) Foreign Application Priority Data

Jul. 10, 2010 (EP) .................................... 10007139

(51) Int. Cl.
*A61B 5/145* (2006.01)
*A61B 17/34* (2006.01)
(Continued)

(52) U.S. Cl.
CPC ......... *A61B 5/14503* (2013.01); *A61B 5/14532* (2013.01); *A61B 17/3403* (2013.01);
(Continued)

(58) Field of Classification Search
CPC .............. A61M 5/158; A61M 5/3287; A61M 2005/1585; A61M 5/425; A61M 2005/1587; A61B 5/14504; A61B 5/14532; A61B 17/3403; A61B 2017/3407; A61B 2017/3409
USPC ............. 606/181–185; 604/44, 264, 272, 506
See application file for complete search history.

(56) References Cited

U.S. PATENT DOCUMENTS 7,052,483 B2 * 5/2006 Wojcik ........................ 604/162
7,318,816 B2 1/2008 Bobroff et al.
2005/0182483 A1 * 8/2005 Osborne et al. ............. 623/1.24

(Continued)

FOREIGN PATENT DOCUMENTS

| WO | WO 2005/063115 A1 | 7/2005 | |
| WO | WO 2008/114223 A1 | 9/2008 | |
| WO | WO 2008/131440 | * 10/2008 | .............. A61M 5/32 |
| WO | WO 2008/136310 A1 | 11/2008 | |

OTHER PUBLICATIONS

International Preliminary Report on Patentability for PCT/EP2011/003140, dated Jan. 17, 2013.

*Primary Examiner* — Sarah W Aleman
(74) *Attorney, Agent, or Firm* — Bose McKinney & Evans LLP

(57) ABSTRACT

An insertion device with an underside for placing on the skin of a patient, which has a recess for an insertion needle. The insertion device has means for forming a skin surface rising like a step or slope and facing towards the recess, preferably bearing on the recess. The means for forming the step or slope may include first and second pressure areas for pressing the skin with the recess for the needle located between the first and second pressure areas. The device may be configured whereby a downwardly extending cutting plane, in which the insertion needle lies, intersects the first pressure area in a first line and the second pressure area in a second line, and wherein the first line in the vicinity of the recess extends at a greater height than the second line. At least one of the two pressure areas may be a strip.

19 Claims, 13 Drawing Sheets

(51) Int. Cl.
*A61M 5/158* (2006.01)
*A61M 5/42* (2006.01)

(52) U.S. Cl.
CPC ............ *A61B17/3468* (2013.01); *A61M 5/158* (2013.01); *A61M 5/425* (2013.01); *A61B 2017/3407* (2013.01); *A61B 2560/063* (2013.01); *A61M 2005/1585* (2013.01)

(56) References Cited

U.S. PATENT DOCUMENTS

| | | |
|---|---|---|
| 2006/0036144 A1 | 2/2006 | Brister et al. |
| 2007/0249922 A1 | 10/2007 | Peyser et al. |
| 2008/0015624 A1* | 1/2008 | Sonoda et al. ............... 606/185 |
| 2010/0137799 A1 | 6/2010 | Imai |

\* cited by examiner

METHOD AND DEVICE FOR PUNCTURE OF INSERTION NEEDLE INTO SUBCUTANEOUS FATTY TISSUE

RELATED APPLICATIONS

This application is a continuation application of International Application PCT/EP2011/003140, filed Jun. 24, 2011, which claims priority to EP 10007139.8, filed Jul. 10, 2010, both of which are hereby incorporated herein by reference.

BACKGROUND

The invention relates to an insertion device. An example of an insertion device is known from WO 2008/136310 A1.

Sensors for in-vivo measurement of analyte concentrations, for example of the glucose concentration, are inserted into subcutaneous fatty tissue of a patient by piercing a needle into the fatty tissue. As a general rule, common insertion needles are designed as hollow needles or V-shaped chutes, with a sensor, for example an electrode system for electrochemical measurements, being positioned therein. After the puncture, the insertion needle is pulled out of the body tissue while the sensor stays in the puncture wound produced.

Usually, insertion devices consist of a basic unit which is placed onto the body of a patient and a lancet device which is coupled to the basic unit for insertion purposes and is, subsequently, removed. There are also insertion devices which consist of only a lancet device.

Insertion systems are often handled by patients themselves in order to insert sensors for the measurement of glucose concentration. For this reason, a constant objective in the development of insertion systems is that they can be handled as easily and safely as possible, anchor sensors reliably in fatty tissue, and allow precise measurements. In addition, the pain connected with the puncture of an insertion needle should be minimized as far as possible.

SUMMARY

The insertion devices disclosed herein provide an improved insertion device.

Whereas conventional insertion devices are simply placed onto the skin of a patient and, subsequently, pierce an insertion needle into subcutaneous fatty tissue at a slanted angle or vertically in relation to the skin surface, the embodiments disclosed herein provide that, prior to triggering a puncture, the puncture site is prepared by deforming the skin and, therein, erecting a skin area such that it is rising in the manner of a step or slope. When a puncture is made, an insertion needle can then impinge on the skin area that is rising in the manner of a step or slope at a steep angle, ideally at an essentially vertical angle, and penetrate into the fatty tissue along a relatively great length before there is the risk of an injury to muscular tissue. Thus the skin surface and the fatty tissue below it are shaped to prepare for an insertion, in order to generate advantageous conditions for a puncture.

In order to prepare a puncture of an insertion needle into subcutaneous fatty tissue, a lower side of the insertion device can, for example, be pressed against the skin, wherein the lower side comprises two pressure areas between which a recess for an exit of the insertion needle is disposed and which are arranged at different heights. This means that a sectional plane which extends from the top down and in which the needle is located intersects the first pressure area in a first line and the second pressure area in a second line. The first line in the neighborhood of the recess then runs at a greater height than the second line. When the insertion device is pressed against the patient, the skin in the neighborhood of the recess and the fatty tissue thereunder are compressed to a greater extent in the second pressure area than in the first pressure area. For this reason, a skin area rising in the manner of a step or slope forms in the vicinity of the recess, with the insertion needle contained in the insertion device pointing to the skin area.

The two pressure areas may be planar. An area in which the recess for the insertion needle is arranged can be provided between the two pressure areas on the lower side of the insertion device, this area, for example, rising in the manner of a step or ramp. It is also possible that the two pressure areas are curved areas which are adjacent to each other at the recess.

A compressing of tissue is advantageous in that the skin can, then, be pierced more easily, but it is not necessarily required. For example, the skin can be bulged by affixing an adhesive area to the skin to be deformed and, subsequently, pulling this adhesive area upwards. It is, however, also possible to cause or support a bulging of the skin by exerting pressure, with the result that tissue is compressed therein. One side of the bulging skin forms a surface that is rising in the manner of a slope and allows an advantageous insertion. This means that the means for forming a skin area rising in the manner of a step or slope can, for example, be designed as means for generating a bulging of the skin.

In some embodiments, at least one of the two pressure areas is a strip. A long narrow pressure area can be pressed into the skin with less force such that there is a step or skin slope forming for a puncture. Preferably, the longitudinal direction of the strip extends in the direction of the insertion needle, i.e. in the piercing direction. Preferably, the width of the strip is less than 1 cm, for example 0.5 cm to 0.7 cm. Preferably, the length of the strip is more than twice its width, more preferably at least four times its width, for example 2 cm to 5 cm.

In general, an insertion needle can more easily pierce through the skin the steeper the angle is at which it impinges on the skin. At the end of an insertion method, a normal to the surface of the skin at the point to which the insertion needle points with its tip, therefore, preferably forms an angle with the insertion needle of less than 30°, more preferably less than 20°, most preferably less than 10°.

In one embodiment of a method according to the invention, the skin surface is, preferably, deformed by the effect of the insertion device at least to such an extent that a normal to the surface at a point of the rising surface to which the insertion needle points includes an angle with a normal to the surface at the same point of the skin surface prior to deforming of at least 45°, preferably of at least 60°.

Preferably, the insertion needle is held in the insertion device in a direction that extends obliquely from the top down, which means that it extends at a slanted angle in relation to the lower side of the insertion device. Herein, the terms "down" and "top" refer to the insertion device, wherein the lower side of the insertion device is the side that is seated on the skin of the patient during a puncture or after completion of the insertion method. Accordingly, the upper side of the insertion device is the side that is facing away from the skin of the patient during a puncture or after completion of the insertion method.

An insertion device according to the invention has means for forming a skin area rising in the manner of a step or slope which faces the recess provided for the exit of the insertion needle. This means that the insertion device forms the skin such that a skin area is erected in the manner of a step or slope and is then facing the recess, for example an outlet opening.

Preferably, the skin is formed by an exemplary insertion device such that the skin area rising in the manner of a step or slope rests against the recess because, in this manner, the puncture site is defined particularly well.

The means for forming a skin area rising in the manner of a step or slope can, for example, be means for maintaining a bulging of the skin of the patient. An insertion needle contained in the insertion device is, preferably, oriented at a slanted angle in relation to a resting or pressure area of the insertion device, next to which the bulging is generated. This means that the insertion needle points in a direction which includes an acute angle with a planar resting or pressure area, this angle, for example, ranging from 2° to 45°, more particularly from 20° to 45°. Since, usually, insertion needles extend in a straight direction, the insertion needle then includes an acute angle with the resting area as well. As such, the resting or pressure area can also be somewhat rounded, for example adjusted to the natural curvature of a belly. In such a case, the slanted orientation of the insertion needle means that a tangential extension of the area intersects the direction into which the insertion needle points at an acute angle.

The means used for forming the skin can, for example, be two holding parts which are movable against each other and between which a bulging of the skin is seized.

If two holding parts that are movable against each other are used to generate and hold a bulging of the skin, these holding parts preferably each comprise a pressure area for the bulging of the skin. Preferably, the insertion needle points along at least one of the pressure areas, being spaced apart therefrom. During a puncture, the insertion device then pushes the insertion needle along the pressure area spaced apart therefrom, preferably in a direction extending essentially parallel to the pressure area. The insertion needle can, thus, be pushed into subcutaneous fatty tissue in parallel to the skin surface.

It is possible that the pressure area of the other holding part comprises a recess, e.g. an opening for the insertion needle. It is, however, also possible that the insertion needle points through between the two pressure areas, i.e. that, during a puncture, the insertion needle is moved past the two pressure areas spaced apart therefrom.

An advantageous refinement of the invention provides that the insertion device is composed of a first and a second partial body wherein the first and second partial bodies are movable against each other and a slit extends between the first and second partial bodies and through the recess provided for the exit of the insertion needle. By the two partial bodies being movable against each other, the slit extending through the recess can be enlarged after a puncture, so that the insertion device can be removed from the patient more easily, for example in order to facilitate the handling of a sensor patch connected to the sensor. Sensors are often connected to what is called a sensor patch which is adhered to the skin of the patient after the insertion of a sensor. A sensor patch can, for example, contain a potentiostat for supplying an electrode system forming the sensor with energy, a battery and/or control electronics.

Preferably, the two partial bodies can be removed from each other. However, the slit extending between said partial bodies can, for example, also be broadened by a swivel movement of the two partial bodies against each other to such an extent that a sensor patch that is connected to the inserted sensor can be placed on the skin of the patient.

BRIEF DESCRIPTION OF THE DRAWINGS

The above-mentioned aspects and further details and advantages of exemplary embodiments will become more apparent and will be better understood by reference to the following description of the embodiments taken in conjunction with the accompanying drawings. Therein, parts that are equal or correspond to each other are provided with consistent reference symbols. In the drawings.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of these teachings.

Figure 1:
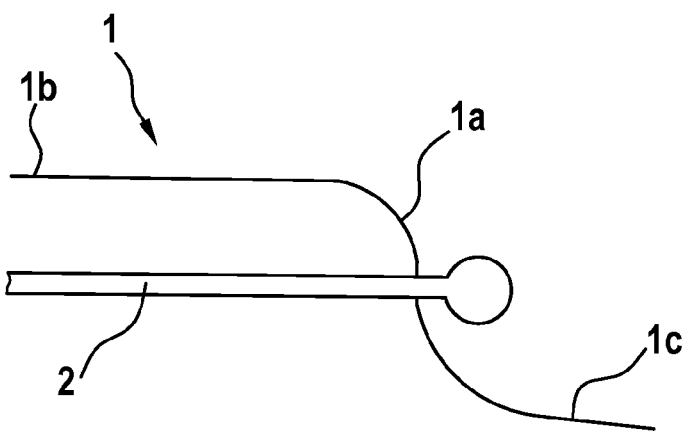
FIG. 1 is a schematic representation of a bulged skin surface with an inserted sensor.

FIG. 1 shows a skin surface 1 with an inserted sensor 2. A skin area 1a is rising in the manner of a step or slope having been generated in the skin surface 1 by deformation. The sensor 2 projects from the skin area 1a rising in the manner of a step or slope and extends in the subcutaneous fatty tissue in essence in parallel to the skin area 1b which is disposed thereupon and, at its top, is adjacent to the skin area 1a rising in the manner of a step or slope at the top.

Figure 2:
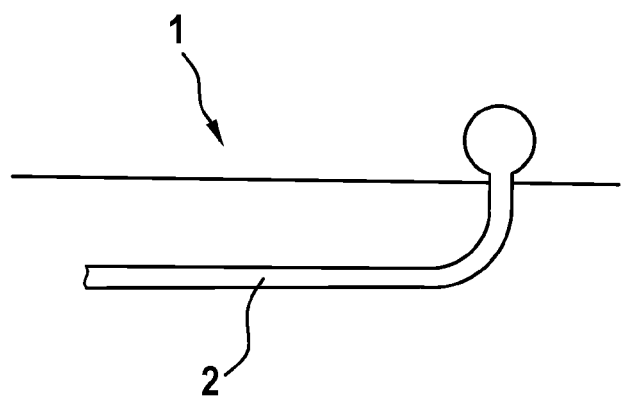
FIG. 2 shows the skin surface shown in FIG. 1 in its relaxed state and with inserted sensor.

A step- or slope-like rise is only preserved as long as a corresponding force acts on the skin surface 1 and accordingly deforms the skin surface 1 with the fatty tissue disposed thereunder. Once such a force is not in effect any longer, for example because the insertion device causing the deformation has been removed from the skin surface 1, the skin surface 1 relaxes and returns into its natural state that is approximately flat and whereby a sensor inserted in the subcutaneous fatty tissue is bent as shown in FIG. 2. The section of the sensor previously extending in parallel to the skin area 1b is oriented approximately in parallel to the skin surface 1 even with the skin surface 1 being relaxed and can, therefore, extend along an advantageously great length in fatty tissue under the skin.

This means that, in order to prepare a puncture of an insertion needle into subcutaneous fatty tissue of a patient by means of an insertion device, the skin is deformed by an effect of the insertion device and a skin area is arranged such that it is rising in the manner of a step or slope and an insertion needle held in the insertion device points to the skin area 1a rising in the manner of a step or slope.

A normal to the surface of the skin area 1 in the point to which the insertion needle points defines an angle with a theoretical prolongation of the insertion needle of, for example, less than 30°, ideally an angle of 0°. The insertion needle is therefore oriented at a slanted angle in relation to the skin surface 1b, 1c next to the skin area 1a rising in the manner of a step or slope. This means that, in relation to normals to the skin surface 1b, 1c next to the bulging of the skin, the insertion needle defines a larger angle, for example an angle ranging from 30° to 60°.

In order to prepare an insertion of a sensor by means of an insertion device, a skin area 1a rising in the manner of a step or slope can be generated in various ways. Below, a few illustrative embodiments of insertion devices will be explained, which can be used to generate a skin area 1a rising in the manner of a step or slope and maintain it for the duration of an insertion process.

Figure 3:
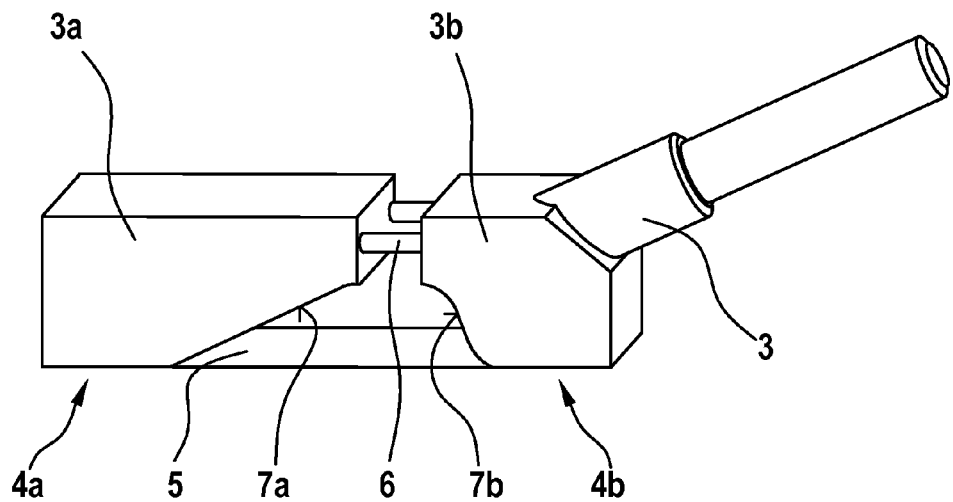
FIG. 3 is a schematic representation of an illustrative embodiment of an insertion device in an initial state provided for being placed onto the skin of a patient.

FIG. 3 shows an illustrative embodiment of an insertion device 3 in its initial state, in which the device 3 is placed onto the skin of a patient. The insertion device 3 has two holding parts 3a, 3b which are movable against each other in order to generate a bulging of the skin with a skin area rising in the manner of a slope and maintain it subsequently. The two holding parts 3a, 3b each have a pressure area 4a and 4b, respectively, with which the insertion device 3 is pressed against the skin of a patient in order to prepare an insertion. An adhesive film 5 is fastened to the two holding parts 3a, 3b. The adhesive film 4 therefore bridges a groove between the two holding parts 3a, 3b. In the illustrative embodiment shown, the holding parts 3a, 3b are movable against each other by being pushed and, to achieve this, connected to each other via a linear guide 6, for example one or a plurality of guiding rods.

Figure 4:
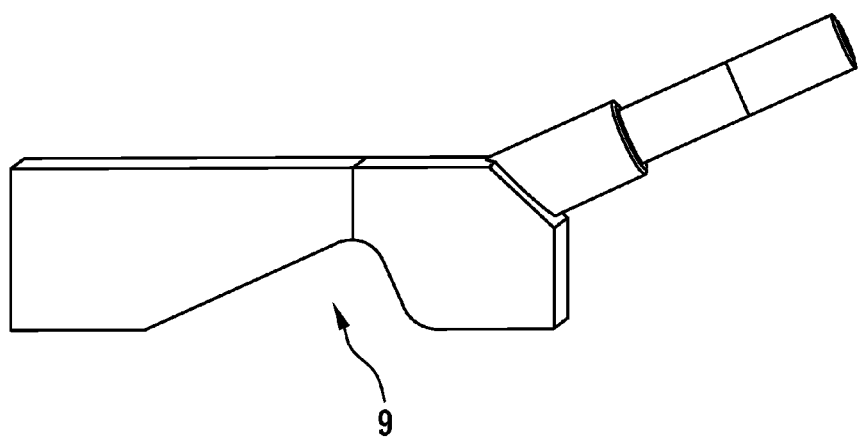
FIG. 4 shows the insertion device shown in FIG. 3 in a final state for holding a bulging of the skin.
Figure 5:
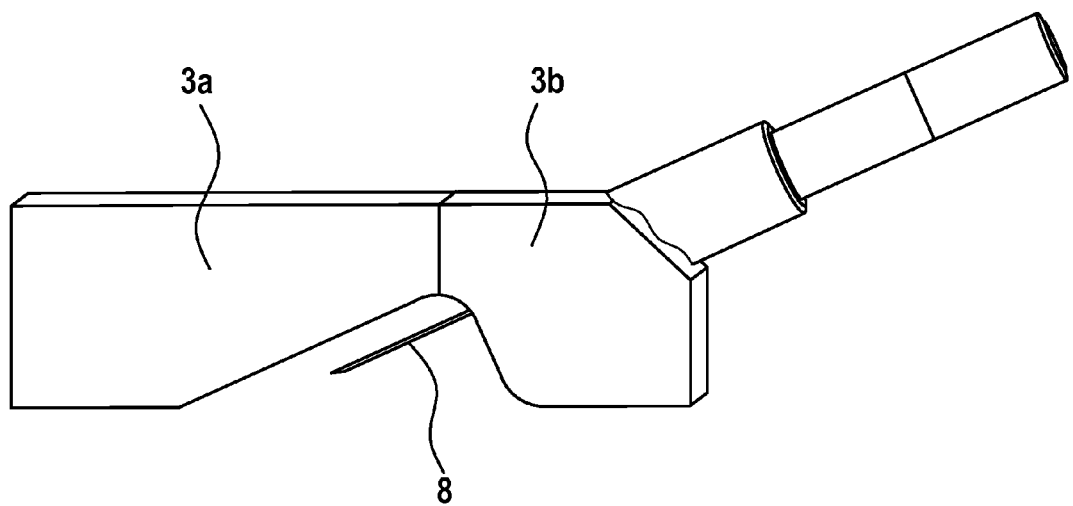
FIG. 5 shows the insertion device shown in FIG. 4 with protruding insertion needle.

In order to generate a bulging of the skin, the two holding parts 3a, 3b are pushed together into the final state shown in FIGS. 4 and 5. Therein, the adhesive film 5 and, therefore, the skin adhered to it as well, are bulged up, with the result that the adhesive film 5 rests against the resting areas 7a, 7b of the holding parts 3a, 3b and a bulging 9 of the skin is seized by the partial bodies 3a, 3b. The sides of the bulging 9 of the skin are skin areas rising in the manner of a slope.

In the illustrative embodiment shown, the holding part 3b supports the insertion needle 8. A part of the insertion device that contains the insertion needle 8 can be permanently connected to the first holding part 3a or be applied to the first holding part 3a only for the actual insertion process, i.e., the puncture.

In the illustrative embodiment shown, the resting area 7b of the holding part 3b has a recess, that is an opening for the insertion needle 8 shown in FIG. 5. When a puncture is made, the insertion needle 8 impinges on a lateral surface of the bulging 9 of the skin, preferably almost vertically, and then moves under a flat angle, preferably in parallel, to an opposite lateral surface of the bulging 9 of the skin which rests against the resting area 7a of the holding part 3a. In the illustrative embodiment shown, the insertion needle 8 is, in essence, slid into subcutaneous fatty tissue in parallel to the resting area 7a of the holding part 3b.

In an insertion device 3 which consists of two holding parts 3a, 3b that can be pushed against each other, as is the case in the illustrative embodiment shown, the resting area 7b of the holding part 3b supporting the insertion needle 8, preferably, has a smaller length than the resting area 7a of the other holding part 3a. Therein, the length of the resting areas 7a, 7b is each to be measured from the neighboring pressure area 4a and 4b, respectively, in the direction towards the other holding part. Preferably, the longer resting area 7a is at least twice as long as the shorter resting area 7b.

Preferably, the pressure areas 4a, 4b of the two holding parts 3a, 3b are, in essence, planar and oriented in parallel to each other. In the illustrative embodiment shown, the resting areas 7a, 7b for forming and holding a bulging of the skin are, in essence, planar, too, but can also be curved. Starting from the pressure areas 4a, 4b, the resting areas 7a, 7b rise upwards, with the result that they limit a recess on the lower side of the insertion device 3, which can receive a bulging of the skin. The pressure areas 4a, 4b are each formed as straight-line strips.

When the insertion device 3 is placed onto the skin surface 1 of a patient, the insertion needle 8 initially points at a slanted angle to a point of the not yet bulging skin surface. This means that, in this point of the skin surface 1, a theoretical prolongation of the insertion needle 8 in the direction of the puncture defines a first angle with a normal to the surface of, for example, 30° to 60°. After the bulging of the skin has been generated, the insertion needle 8 points to a lateral side of the bulging of the skin, i.e. to the skin area rising in the manner of a slope. A normal to the surface of the skin area in the point to which the insertion needle 8 points then defines a second angle with a theoretical prolongation of the insertion needle 8 in the direction of the puncture, this second angle being smaller than the first angle and, preferably, less than 30°, more preferably less than 20°. In an ideal situation, the insertion needle 8 points vertically to the skin area rising in the manner of a slope.

Figure 6:
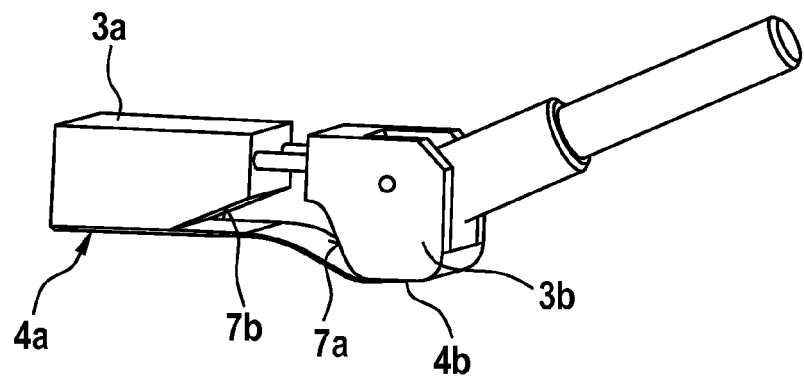
FIG. 6 is a schematic representation of a further illustrative embodiment of an insertion device in an initial state.

FIG. 6 schematically shows a further illustrative embodiment of an insertion device 3 in its initial state in which the insertion device 3 can be placed onto the body of a patient. In essence, the illustrative embodiment shown in FIG. 6 differs from the embodiment described above only in that the two pressure areas 4a, 4b are arranged at different heights and offset in relation to each other. For this reason, a theoretical prolongation of the pressure area 4a of the holding part 3a intersects the resting area 7b of the holding part 3b which comprises the opening 11 for the insertion needle 8.

When the insertion device 3 is pressed onto the skin of a patient, the tissue in the vicinity of the skin area rising in the manner of a slope is compressed to a greater extent by the offset arrangement of the two pressure areas 4a, 4b. This is advantageous in that the tissue can give way to a lesser extent and a sensor 2 can be placed more precisely in the subcutaneous fatty tissue during the puncture of the insertion needle 8.

Figure 8:
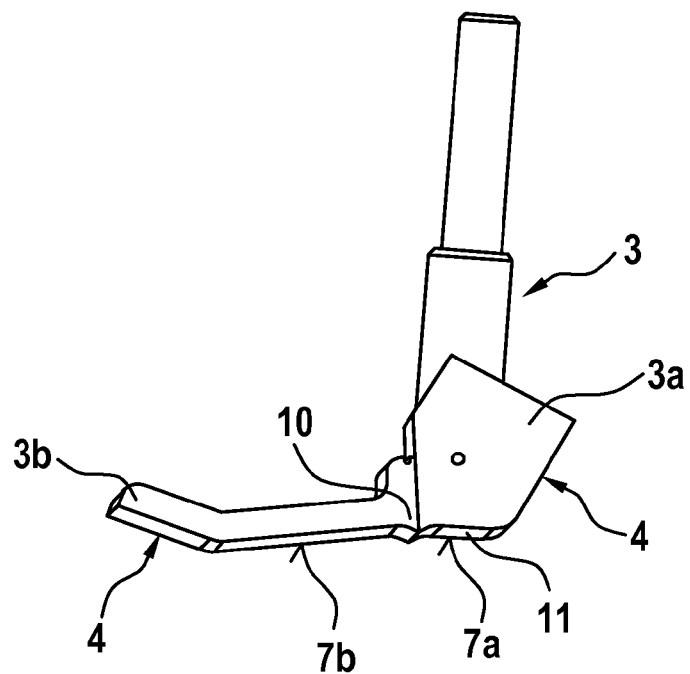
FIG. 8 is a schematic representation of a further illustrative embodiment of an insertion device in an initial state.
Figure 9:
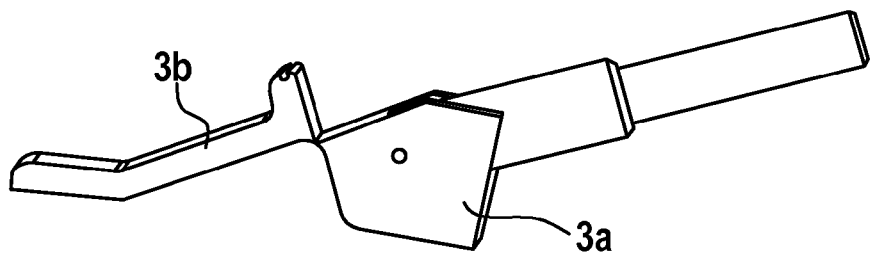
FIG. 9 shows the insertion device shown in FIG. 8 in a final state that is provided for holding a bulging of the skin.

A further illustrative embodiment of an insertion device 3 is shown in FIG. 8 in its initial state for being placed onto the skin of a patient and in FIG. 9 in its final state that is provided for holding a bulging 9 of the skin. In essence, this illustrative embodiment differs from the embodiment of FIGS. 3 to 5 in that the two holding parts 3a, 3b are movable against each other in a swiveling manner. At first, the insertion device 3 is placed onto the skin of a patient with the two resting areas 7a, 7b. The two resting areas 7a, 7b are adhesive areas, for example by the holding parts 3a, 3b being covered with an adhesive film 5 at this point. Thereafter, the holding part 3a is swiveled against the other holding part 3b, with the result that the holding parts each press against the skin of the patient with their pressure areas 4. The skin adhered to the resting areas 7a, 7b is pulled upwards and, therefore, a bulging 9 of the skin is generated and held between the two holding parts 3a, 3b. The bulging 9 of the skin forms a skin area that rises in the manner of a slope and rests against an opening 11 for the insertion needle, the opening 11 being present in the resting area 7a.

The two holding parts 3a, 3b can be connected to each other via a film hinge 10 which can, for example, be formed by the adhesive film covering the resting areas 7a, 7b.

Figure 10:
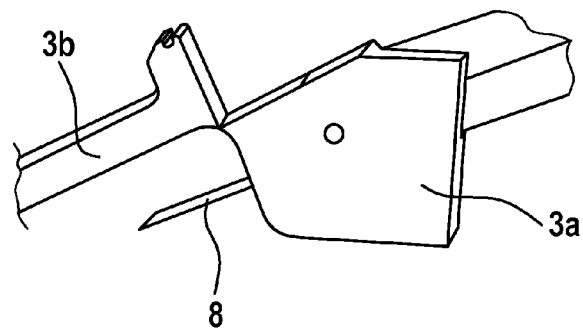
FIG. 10 shows the device shown in FIG. 9 with protruding insertion needle.

FIG. 10 shows a detail of the insertion device 3 shown in FIG. 9, with a protruding insertion needle 8. As is evident, the orientation of the insertion needle 8 with respect to the pressure areas 4 and the resting areas 7a, 7b does not differ from the geometrical conditions of the embodiment shown in FIG. 5.

Figure 11:
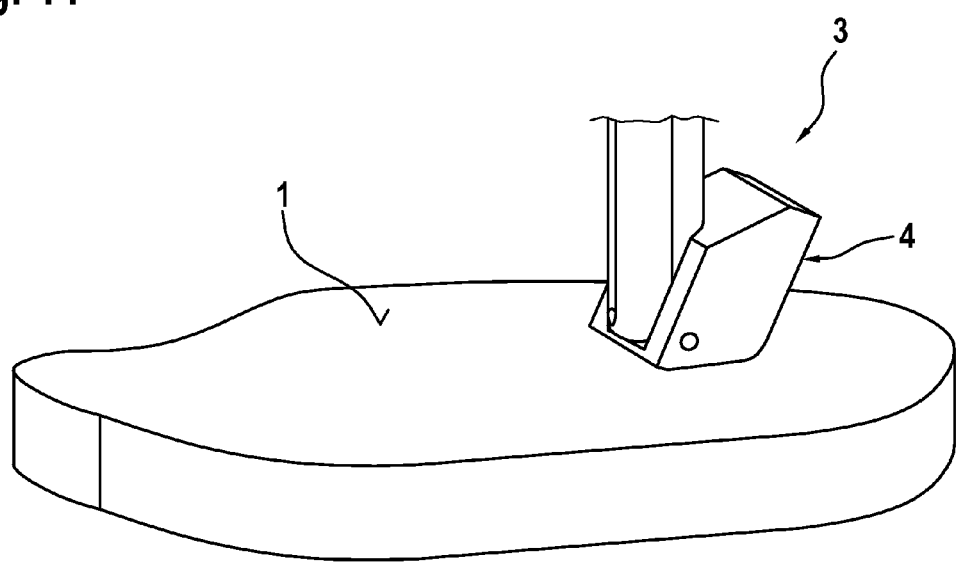
FIG. 11 is a schematic representation of a further illustrative embodiment of an insertion device with a skin surface.
Figure 12:
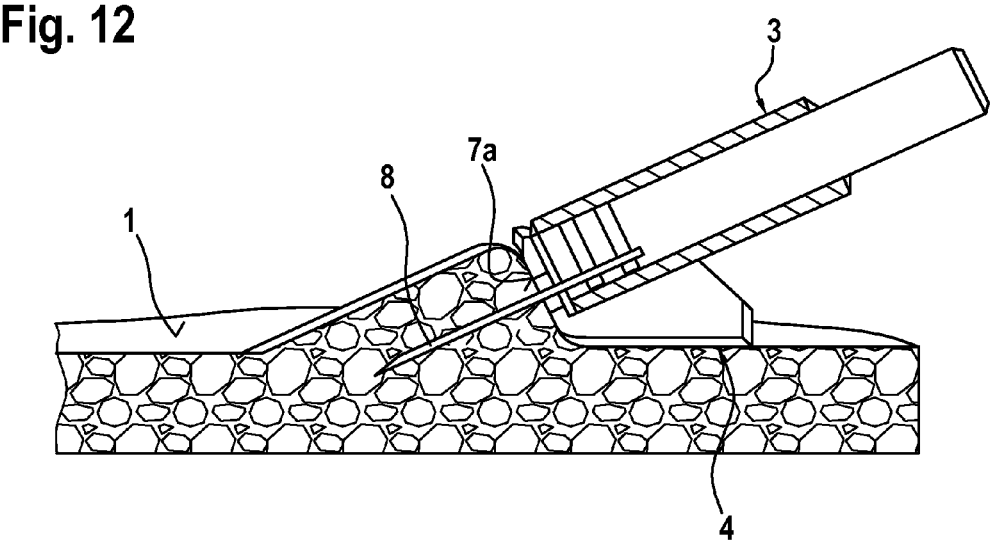
FIG. 12 is a schematic lateral view of the insertion device shown in FIG. 11 with a bulging of the skin.

FIGS. 11 and 12 show a further illustrative embodiment of an insertion device 3 with a skin surface 1. At first, the insertion device 3 is placed onto the skin with the resting area 7a which is formed as an adhesive area and comprises an opening for the insertion needle. Thereafter, the insertion device 3 is tilted over from the initial position shown in FIG. 10 to the final position shown in FIG. 11, with the result that a pressure area 4 of the insertion device 3 is pressed against the skin 1. In the embodiment shown in FIG. 11, the pressure area 4 defines an obtuse angle with the resting area 7a. Since the skin 1 adheres to the resting area 7a, the tilting of the insertion device to the final position shown in FIG. 12 generates a bulging 9 of the skin, into which a puncture with an insertion needle 8 can be made thereafter.

Figure 13:
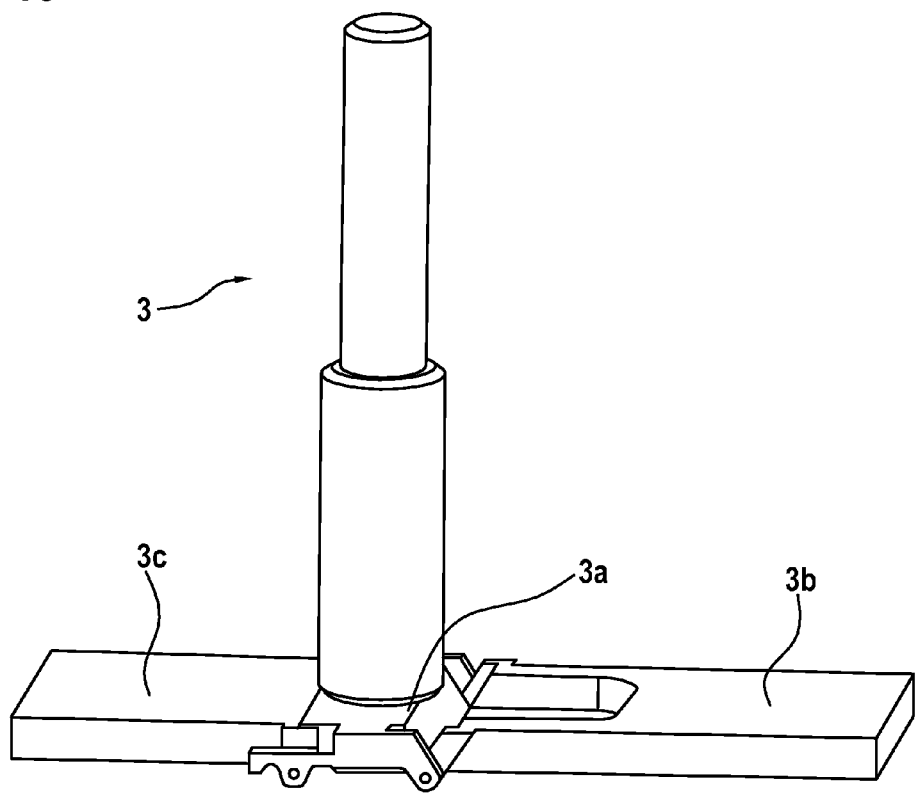
FIG. 13 is a schematic representation of a further illustrative embodiment of an insertion device in an initial state.
Figure 14:
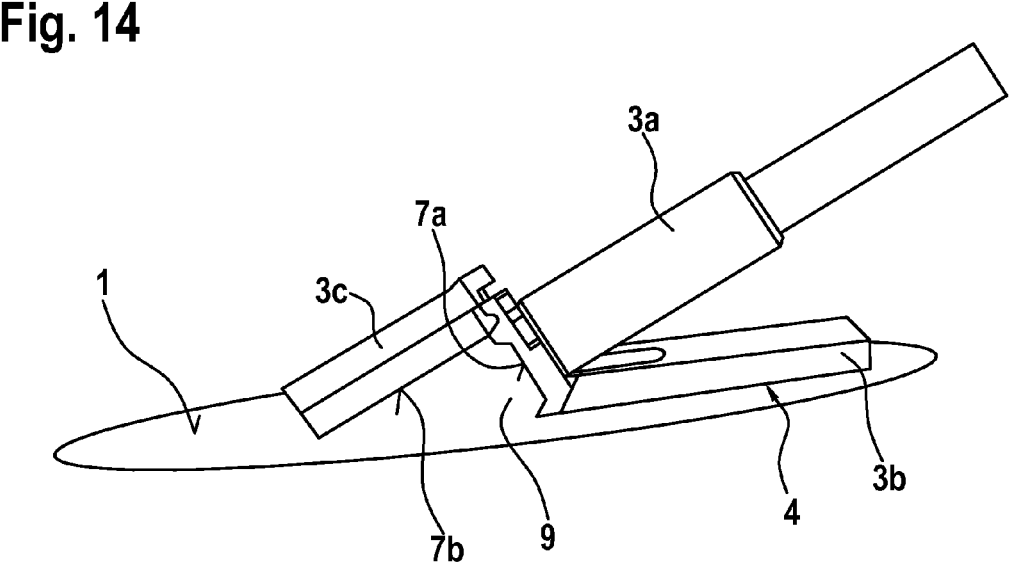
FIG. 14 shows the insertion device shown in FIG. 13 with a generated bulging of the skin.

FIG. 13 shows a further illustrative embodiment of an insertion device 3 in which the means for generating and holding a bulging 9 of the skin comprise holding parts 3a, 3b, 3c that are movable against each other. The holding parts 3b and 3c are attached to the holding part 3a in a swiveling manner. In the initial state shown in FIG. 13, the insertion device 3 is placed onto the skin of a patient. Thereafter, the holding part 3a is tilted similarly to the embodiments described above. The two holding parts 3b and 3c are swiveled to the final state shown in FIG. 14. The holding part 3b comprises the resting area 4 with which the insertion device 3 is pressed against the skin. The holding part 3a forms a resting area 7a for the bulging 9 of the skin and comprises an opening for the insertion needle. The holding part 3c forms a resting area 7b which rests on the other side of the bulging 9 of the skin.

Figure 15:
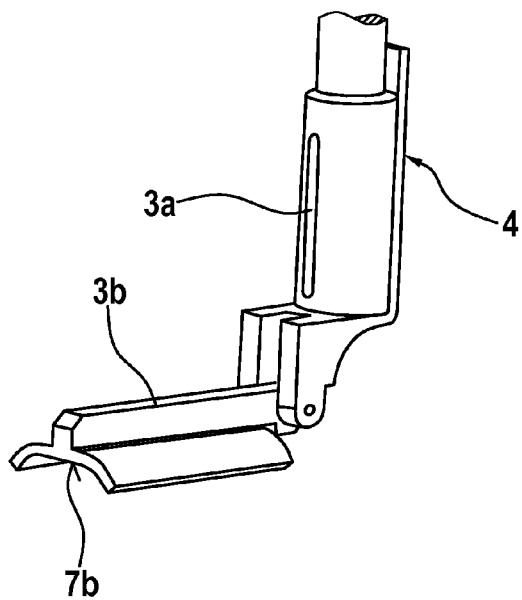
FIG. 15 is a schematic representation of a further illustrative embodiment of an insertion device in an initial state.
Figure 16:
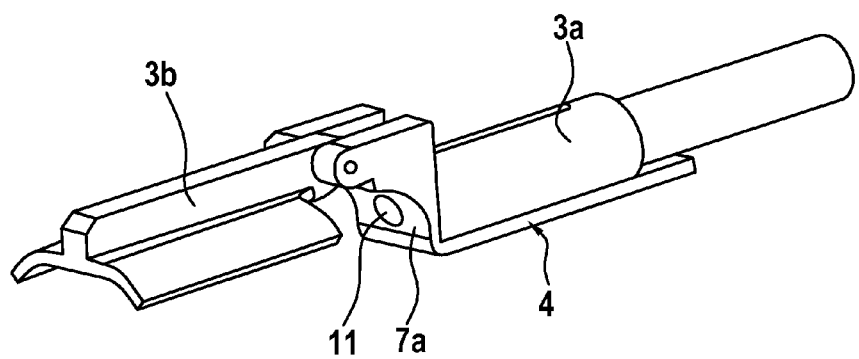
FIG. 16 shows the insertion device shown in FIG. 15 in a final state.

A further illustrative embodiment of an insertion device 3 is shown in FIG. 15 in its initial state in which it is placed onto the skin of a patient and in FIG. 16 in its final state that is provided for holding a bulging 9 of the skin. This embodiment also comprises two holding parts 3a, 3b that are movable against each other as means for generating and holding a bulging 9 of the skin. At first, the device is placed onto the skin of a patient with the resting area 7b of the second holding part 3b. The resting area 7b is formed as an adhesive area, for example by means of an adhesive film 5. Thereafter, the holding part 3a is swiveled in relation to the holding part 3b, with the result that the holding part is pressed against the skin of the patient with its pressure area 4. Therein, the holding part 3a is moved upwards and the holding part 3a is pressed down, respectively, with the result that a difference in height and, therefore, a skin area rising in the manner of a slope develops between the resting area 7b of the holding part 3b and the pressure area 4 of the holding part 3a.

In the final position shown in FIG. 16, the tip of an insertion needle points through the opening 11 in the resting area 7a of the one holding part 3a and along the resting area 7b of the other holding part 3b being spaced apart therefrom. To trigger a puncture, the insertion needle is slid into subcutaneous fatty tissue in parallel to and along the skin surface resting against the resting area 7b of the second holding part 3b.

Figure 17:
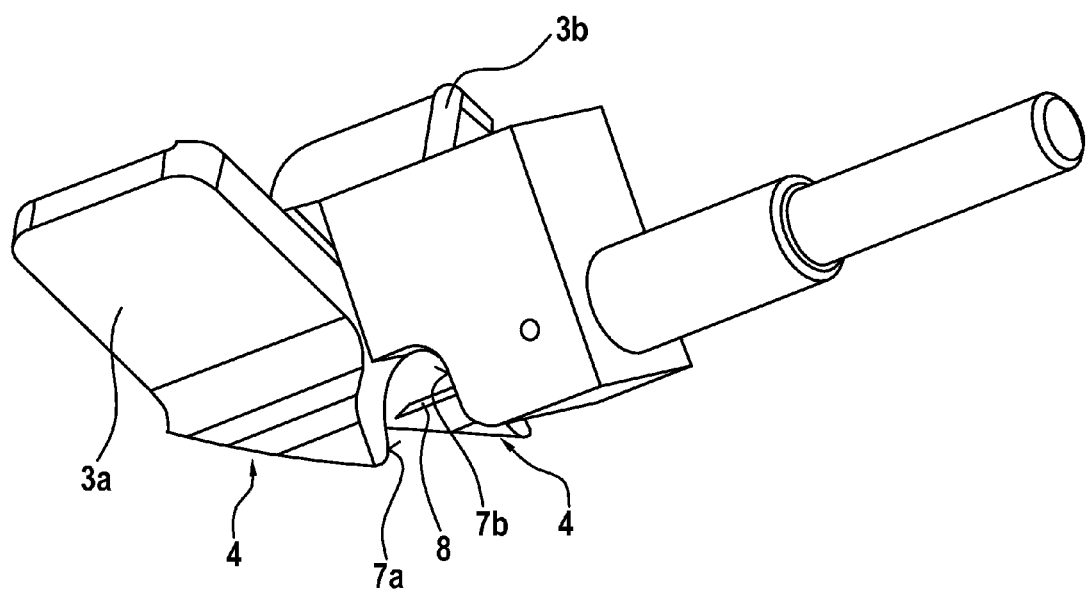
FIG. 17 shows a further illustrative embodiment of an insertion device.

FIG. 17 shows a further illustrative embodiment of an insertion device 3 in which the means for holding and generating a bulging 9 of the skin are formed by two holding parts 3a, 3b of the insertion device 3 that are movable against each other. In the embodiment shown in FIG. 17, the two holding parts are movable against each other in the manner of a clamp and each have a resting area 4 with which the holding parts can be pressed against the skin of a patient. After having been placed onto the skin of a patient, the two holding parts swivel from an initial position to a final position, preferably under the influence of the restoring force of a spring, with the two resting areas 4 having been moved closer to each other and, therefore, having bulged the skin between them in this final state. A generated bulging of the skin then rests against the resting areas 7a and 7b, respectively, of the two holding parts 3a, 3b. In its final position, the insertion needle 8 points along the resting areas 7a, 7b of the two holding parts 3a, 3b spaced apart therefrom, preferably in parallel to and along the resting areas 7a, 7b.

Figure 7:
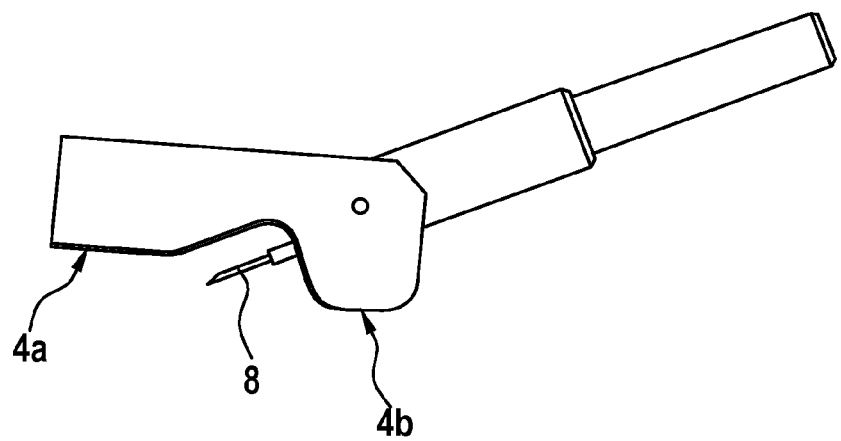
FIG. 7 shows the insertion device shown in FIG. 6 in a final state with protruding insertion needle.
Figure 18:
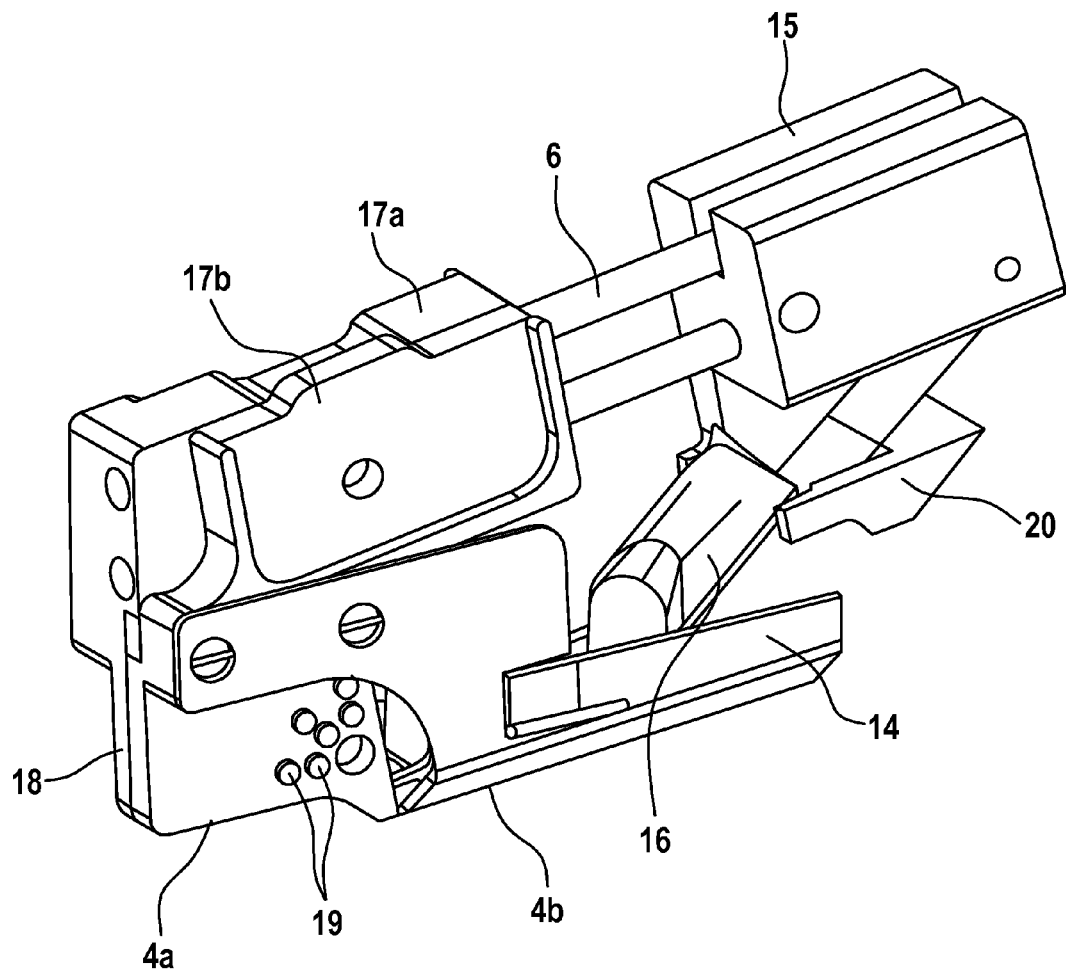
FIG. 18 shows a further illustrative embodiment of an insertion device in an initial state.

A further illustrative embodiment of an insertion needle is shown in FIG. 18. In this embodiment, the skin is deformed by pressing the lower side of the insertion device against the skin. The lower side comprises a first pressure area 4a and a second pressure area 4b, wherein a recess, preferable an opening, for the insertion needle 8 is located between the two pressure areas 4a, 4b. The pressure areas 4a, 4b that are formed as strips are arranged at different heights, similarly to the embodiment of FIGS. 6 and 7. This means that a sectional plane which extends from the top down and in which the insertion needle 8 is positioned intersects the first pressure area 4a in a first line and the second pressure area 4b in a second line and the first line in the neighborhood of the recess extends at a greater height than the second line. Since the aforementioned sectional plane contains the needle 8, the sectional plane also extends through the recess, with the result that there are two lines separated by the recess.

The two pressure areas 4a, 4b can continuously merge in an area rising in the manner of a ramp, in which the recess for the insertion needle 8 is arranged, or can be separated from each other in a defined manner.

When the lower side of the insertion device is pressed against the skin, the subcutaneous fatty tissue is compressed by the pressure areas 4a, 4b. The tissue is compressed by the pressure area 4b that is positioned at a lower height to a greater extent than by the pressure area that is positioned at a greater height, with the result that the skin between the two pressure areas forms an area which rises in the manner of a slope and rests against the outlet opening.

Figure 19:
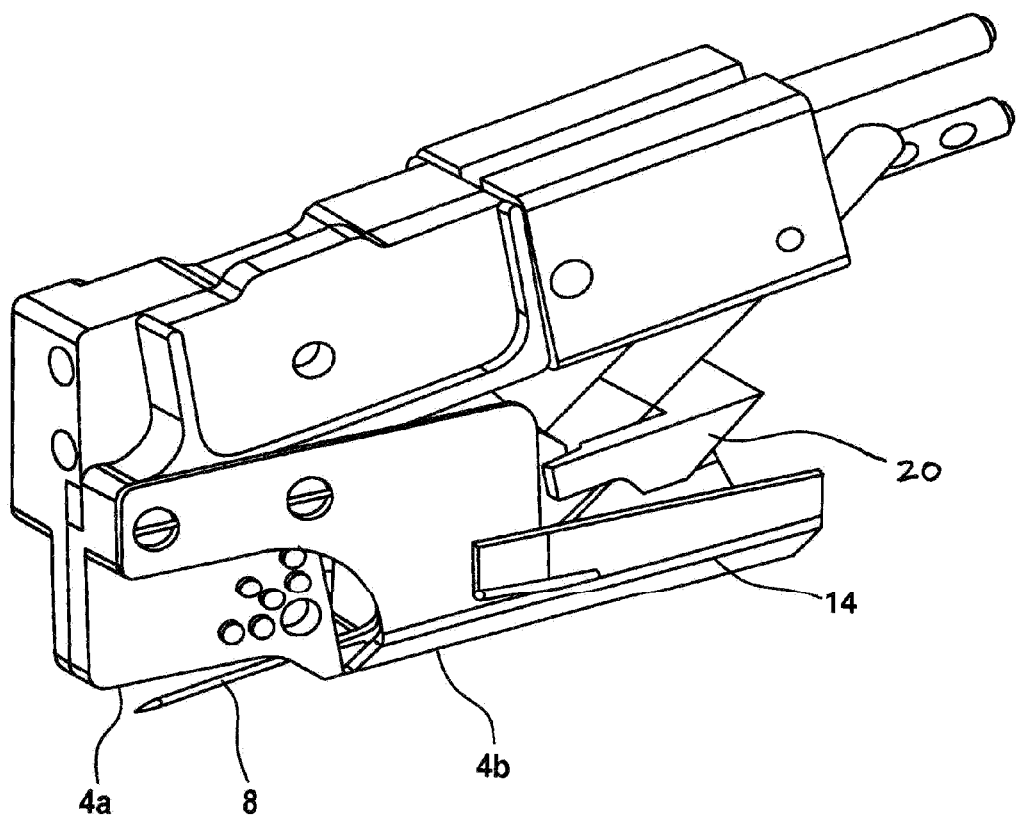
FIG. 19 shows the insertion device shown in FIG. 18 in a final state.

In the embodiment shown, the first pressure area 4a extends further than the insertion needle 8 in the state which is shown in FIG. 19 and is reached at the end of the feed motion when a puncture is made. For this reason, the insertion needle 8 is always covered by the insertion device along its entire length.

The first pressure area 4a is a straight-line strip. Preferably, this strip has a width of less than 1 cm, more preferably of less than 6 mm. In this manner, the pressing force is concentrated on an advantageously small area, with the result that a compression of tissue can be achieved while exerting little force, for example a force of less than 30 N, preferably of less than 20 N, more preferably of 10 N to 20 N. In the embodiment shown, the pressure area 4b is also a straight-line strip having a width of less than 1 cm, for example 0.5 cm to 0.7 cm. When being pressed on, the insertion device, therefore, acts on the skin of a patient in a strip-shaped area. Preferably, the length of this strip-shaped area is at least 2 cm, for example 2.5 cm to 5 cm.

The second pressure area 4b is arranged between two supporting areas which extend both laterally away from the pressure area 4b and upwardly. This means that the insertion device becomes broader in an upward direction, starting at its lower side. When the insertion device is pressed on, the lateral supporting areas 14 act as spacers for displaced tissue, with the result that an increased working space for a piercing mechanism is created.

In the embodiment shown, the piercing mechanism is designed as a slide 15 which, during a puncture, is pushed forward along with the insertion needle 8 it holds. The slide 15 is guided along a linear guide 6 which can, for example, be formed by guiding rods. During a puncture, the slide 15 can move a holder 20 of the sensor patch 16.

Figure 20:
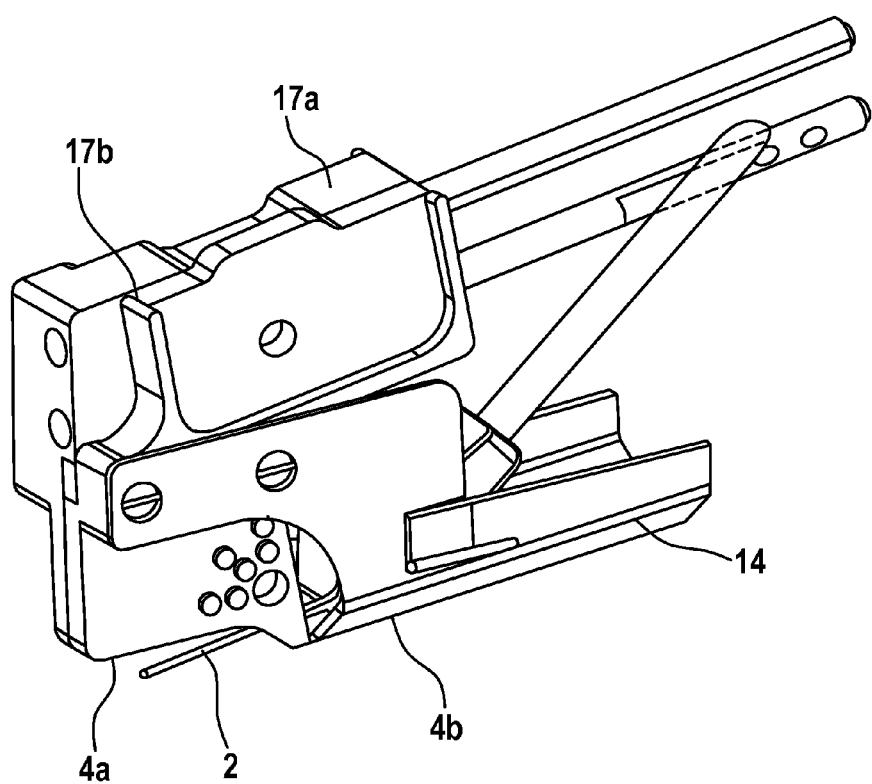
FIG. 20 shows the insertion device shown in FIG. 19 after removal of the first partial body.

After a puncture, the slide 15 is, initially, removed from the insertion device. FIG. 20 shows the insertion device after the slide 15 has been removed.

The insertion device comprises two partial bodies 17a, 17b. A seam 18 extends through the opening between the first partial body 17a and the second partial body 17b. The seam 18 extends in the longitudinal direction of the device, that is through the two pressure areas 4a, 4b. In principle, however, the seam 18 can also extend in transverse direction in relation to the insertion device.

Figure 21:
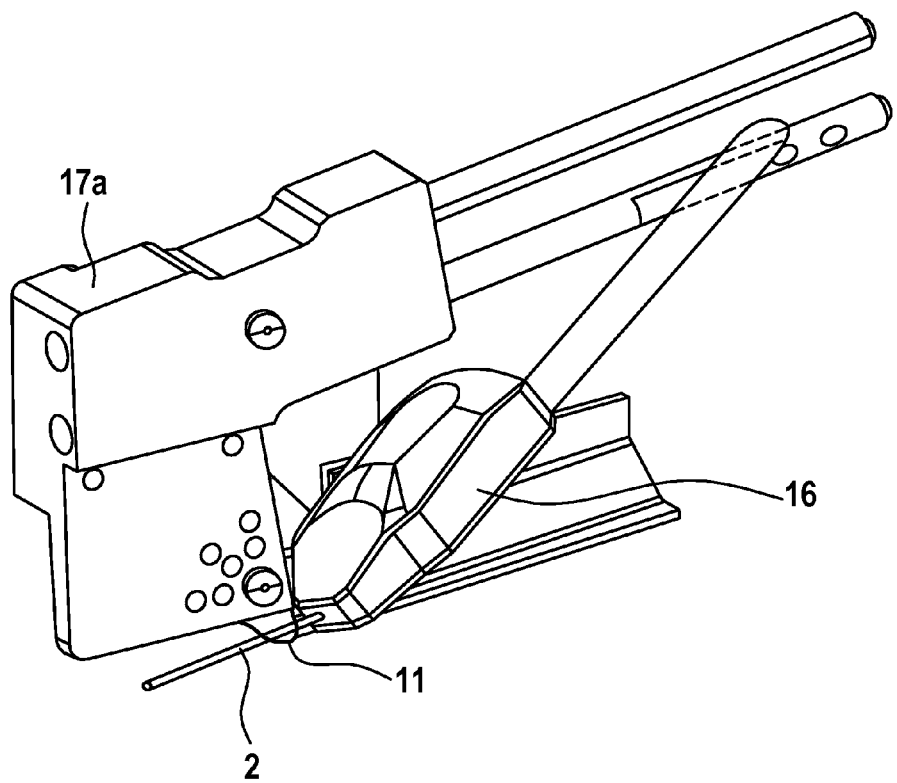
FIG. 21 shows the insertion device shown in FIG. 20 after removal of a lateral supporting area.
Figure 22:
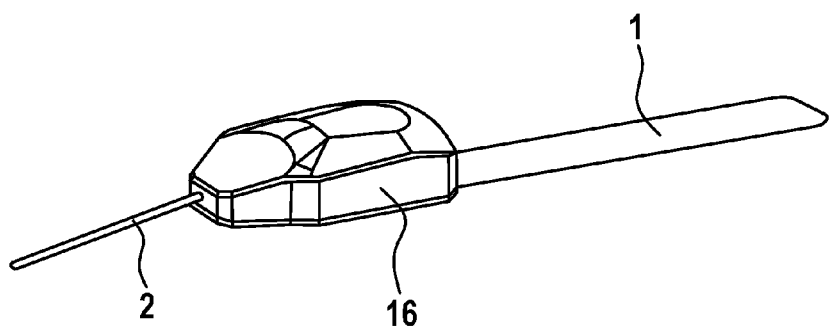
FIG. 22 shows a sensor inserted with the insertion device shown in FIG. 21 and an associated sensor patch.

The two partial bodies 17a, 17b are movable against each other in order that the insertion device can be removed from the body of a patient more easily after the puncture of the insertion needle 8. In the embodiment shown, the first and second partial bodies 17a, 17b are held together by magnetic force. The magnetic force can be overcome manually, with the result that the two partial bodies 17a, 17b can be detached from each other if necessary. FIG. 21 shows the first partial body 17a of the device after the second partial body 17b has been removed. In a further step, the first partial body 17a is removed as well. And thereafter, the sensor patch 16 is adhered to the skin.

In order to connect the two partial bodies 17a, 17b to each other by magnetic force, the two partial bodies 17a, 17b can carry one or a plurality of permanent magnets 19. As such, however, it is sufficient to provide only one of the two partial bodies with a permanent magnet. The other partial body can also carry a soft magnet instead of a permanent magnet, for example by consisting of ferromagnetic steel at the corresponding point.

In order to facilitate manually overcoming the magnetic force for separating the two partial bodies 17a, 17b, one of the two partial bodies 17b can project a little beyond the other partial body 17a on the upper side. In this manner, an area of attack can be formed, for example in order to exert the force required for overcoming the magnetic attraction with one's thumb. It is, however, also possible that the seam 18 between the two partial bodies 17a, 17b broadens in an upward direction in the manner of a wedge or funnel at one point or at a plurality of points. In this manner, it is possible to reach into the seam with one of one's fingers in order to press the two partial bodies 17a, 17b apart.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE SYMBOLS

1 Skin surface
2 Sensor
3 Insertion device
3a Holding part
3b Holding part
3c Holding part
4 Pressure area
5 Adhesive film
6 Linear guide
7a Resting area
7b Resting area
8 Insertion needle
9 Bulging of the skin
10 Film hinge
11 Recess
12 Housing
13 Low-pressure connection
15 Slide
16 Sensor patch
17a Partial body
17b Partial body
18 Seam
19 Magnet
20 Holder

What is claimed is:

1. An insertion device for use with a patient, the insertion device defining a vertical direction, a longitudinal direction perpendicular to the vertical direction and a lateral direction perpendicular to both the vertical and longitudinal directions, the insertion device comprising:
 a lower side adapted to be placed on the skin of the patient and an upper side positioned vertically opposite the lower side, the lower side including a recess for an insertion needle—generally extending in the longitudinal direction and—held by the insertion device;
 means for forming a skin area rising in the manner of a step or slope facing the recess; and
 wherein the means for forming the skin area rising in the manner of a step or slope includes a first pressure area and a second pressure area adapted to be pressed against the skin, wherein the recess for the insertion needle is located between the first pressure area and the second pressure area, and wherein a sectional plane which extends from the upper side in a downward vertical direction to the lower side and in which the insertion needle is located intersects the first pressure area in a first line and the second pressure area in a second line, and wherein the first line runs proximate the recess at a greater vertical height than the second line;

wherein at least one of the two pressure areas is a longitudinally extending strip having a longitudinal length at least twice as great as a lateral width of the strip; and wherein the insertion device broadens in each lateral direction in an upward vertical direction, starting at opposite lateral sides of the lower side.

2. The insertion device according to claim 1 wherein the first pressure area is adapted to be in contact with the skin vertically above the insertion needle when the insertion needle is in a protruding state which is reached at the end of a feed motion when a puncture is made.

3. The insertion device according to claim 2 wherein the strip has a lateral width of less than 1 cm.

4. The insertion device according to claim 2 wherein the second pressure area is a generally planar surface arranged between two supporting areas, the two supporting areas being defined by a pair of inclined surfaces which extend from opposite sides of the second pressure area both laterally away from the second pressure area and vertically upwardly.

5. The insertion device according to claim 1 wherein the strip has a lateral width of less than 1 cm.

6. The insertion device according to claim 5 wherein the second pressure area is a generally planar surface arranged between two supporting areas, the two supporting areas being defined by a pair of inclined surfaces which extend from opposite sides of the second pressure area both laterally away from the second pressure area and vertically upwardly.

7. The insertion device according to claim 1 wherein the second pressure area is a generally planar surface arranged between two supporting areas, the two supporting areas being defined by a pair of inclined surfaces which extend from opposite sides of the second pressure area both laterally away from the second pressure area and vertically upwardly.

8. The insertion device according to claim 7 wherein the second pressure area is a longitudinally extending strip.

9. The insertion device according to claim 1 wherein the means for forming the step- or slope-like skin area comprise an adhesive area adapted to be adhered to the skin to be formed.

10. The insertion device according to claim 1 wherein the means for forming the step- or slope-like skin area of the skin comprises at least two holding parts which are movable against each other in order to form the skin.

11. The insertion device according to claim 1 wherein the insertion device is composed of first and second partial bodies wherein the first and second partial bodies are movable against each other and a vertically and longitudinally extending seam extends between the first and second partial bodies and through the recess and wherein relative movement of the first and second partial bodies facilitates removal of the insertion device after an insertion and each of the first and second partial bodies defines at least a portion of at least one of the first and second pressure areas.

12. The insertion device according to claim 11 wherein the first and second partial bodies are held to each other by magnetic force.

13. The insertion device according to claim 1 wherein the insertion needle is held in the insertion device at a slanted angle in the vertically downward direction relative to the longitudinal direction.

14. The insertion device according to claim 10 wherein the first and second pressure areas are planar and disposed parallel with each other and the longitudinal direction.

15. The insertion device according to claim 1 wherein at least the second pressure area is a strip.

16. The insertion device according to claim 1 wherein the two pressure areas form a strip-shaped area with which the insertion device acts on the skin of a patient when the insertion device is pressed onto the skin.

17. The insertion device according to claim 1 wherein the first and second pressure areas are planar and disposed parallel with each other.

18. An insertion device for use with a patient, the insertion device defining a vertical direction, a longitudinal direction perpendicular to the vertical direction and a lateral direction perpendicular to both the vertical and longitudinal directions, the insertion device comprising:

a lower side adapted to be placed on the skin of the patient and an upper side positioned vertically opposite the lower side, the lower side including a recess for an insertion needle held by the insertion device;

means for forming a skin area rising in the manner of a step or slope facing the recess; and wherein the means for forming the skin area rising in the manner of a step or slope includes a first pressure area and a second pressure area adapted to be pressed against the skin, wherein the recess for the insertion needle is located between the first pressure area and the second pressure area, and wherein a sectional plane which extends from the upper side in a downward vertical direction to the lower side and in which the insertion needle is located intersects the first pressure area in a first line and the second pressure area in a second line, and wherein the first line runs proximate the recess at a greater vertical height than the second line;

wherein at least one of the two pressure areas is a longitudinally extending strip having a longitudinal length at least twice as great as a lateral width of the strip; and wherein the insertion device broadens in each lateral direction in an upward vertical direction, starting at opposite lateral sides of the lower side; and at least one linear guide and a slide body slidingly disposed on the linear guide; the slide body being adapted to support the insertion needle wherein sliding advancement of the slide body advances the insertion needle in a puncture movement.

19. The insertion device according to claim 18 wherein the linear guide comprises a plurality of guide rods.

\* \* \* \* \*